United States Patent [19]

Sampson

[11] Patent Number: 5,061,242
[45] Date of Patent: Oct. 29, 1991

[54] ADJUSTABLE IMPLANTABLE DRUG INFUSION SYSTEM

[75] Inventor: Edward J. Sampson, Carlisle, Mass.
[73] Assignee: Infusaid, Inc., Norwood, Mass.
[21] Appl. No.: 381,350
[22] Filed: Jul. 18, 1989
[51] Int. Cl.[5] .............................................. A61M 1/00
[52] U.S. Cl. .................................. 604/118; 604/141; 604/246
[58] Field of Search ................... 604/9, 65, 32, 118, 604/131, 140, 141, 151, 245-248, 890.1, 891.1; 128/DIG. 12

[56] References Cited

U.S. PATENT DOCUMENTS

| | | | |
|---|---|---|---|
| 4,221,219 | 10/1980 | Tucker | 604/141 |
| 4,299,220 | 11/1981 | Dorman | 604/118 |
| 4,447,224 | 5/1984 | DeCant, Jr. et al. | 128/DIG. 12 |
| 4,486,190 | 12/1984 | Reinicke | 604/891.1 |
| 4,515,588 | 5/1985 | Amendolia | 604/247 |
| 4,838,887 | 6/1989 | Idriss | 604/246 |

Primary Examiner—John D. Yasko
Assistant Examiner—Anthony Gutowski
Attorney, Agent, or Firm—Sughrue, Mion, Zinn, Macpeak & Seas

[57] ABSTRACT

A drug delivery system for implantation into a living body having a pressure actuated infusion pump and an adjustable flow regulator. The regulator comprises a body having a regulator cavity divided by a diaphragm into two chambers. One chamber serves as a pressure sensor and the other as a conduit through which fluid flows. The outlet from the conduit chamber can be sealed by diaphragm movement as a function of pressure increase or the flow restricted. The outlet itself is mounted on an adjustable fitting that is movable relative to the diaphragm. The distance between the outlet and the diaphragm may be set as a calibration of the regulator.

6 Claims, 1 Drawing Sheet

ADJUSTABLE IMPLANTABLE DRUG INFUSION SYSTEM

BACKGROUND OF THE INVENTION

1. Field of the Invention

This invention is directed to a system for accurately controlling the flow rate of a drug from an implantable drug delivery device. One device of this type is the implantable infusion pump described in U.S. Pat. No. 3,731,681. This invention is an improvement over the system disclosed in U.S. Pat. No. 4,299,220 which relates to a compensating mechanism for an implantable pump. These devices are used to deliver drugs at a very slow rate over a long period of time prior to subcutaneous refill.

2. Prior Art

U.S. Pat. No. 3,731,681 describes an implantable infusion pump which utilizes the vapor pressure of a two stage gas to maintain a constant pressure on a drug flowing through a capillary tube in order to maintain a constant flow rate. This technique of flow control while simple and reliable is sensitive to outside variables such as body temperature and atmospheric pressure. Because the temperature of the body in which the device is implanted remains relatively constant, the vapor pressure also stays constant. Thus, while the patient remains at one local ground level air pressure is also essentially constant. However, there are conditions in which both temperature and atmospheric pressure may significantly change. If, for example, the patient has a high fever and at the same time takes a ride in an airplane where the atmosphere pressure is much lower than at sea level the high vapor pressure inside the pump due to the fever and the low pressure outside the pump due to the high altitude will cause pump to flow at a rate about 25% higher than at standard temperature and at sea level. While the drug dosage can be adjusted by changing the concentration of drug in the pump this, never the less, is a serious inconvenience and hardship for the patient.

U.S. Pat. No. 4,299,220 defines an improved implantable pump system employing a regulator to compensate for variations in pressure and temperature and thereby insure a more accurate and uniform rate of drug delivery. The implantable flow regulator of the '220 patent employs a body having a shallow internal cavity and a flexible diaphragm in the body which divides the cavity into two chambers. An inlet is provided to each of the chambers. An outlet is provided leading from the second of the chambers and is centrally disposed in the wall of the cavity underlying the diaphragm. Thus, flexing of the diaphragm in one direction contacts an elastomeric sealing ring around the outlet and closes the fluid passage way. The inlet of the regulator body is adapted to be connected to the capillary flow line from a pressure actuated drug delivery device. The flow line includes at least one capillary restrictor upstream from the inlet to the second chamber. The outlet from the second chamber of the regulator body is adapted to be connected to a catheter flow line extending to the desired infusion cite within the patient.

The capillary restrictor is thus in series with the flow control valve which is formed by the outlet and the diaphragm. The normal pressure drop across the capillary is less than the minimum pressure drop across the entire system, that is the pressure difference between the drug chamber and the distal end of the catheter in the outside environment of the infusion site. The pressure drop across the capillary tube is sensed by the diaphragm. When the opposing forces on the diaphragm are stable, the diaphragm is stationary. If there is a change in these forces, the diaphragm deflects either to close the valve when the pressure difference is negative in the second chamber or to open the valve if the pressure difference is positive in the second chamber.

SUMMARY OF THE INVENTION

This invention is directed to an improvement over the system disclosed in the '220 patent. One of the difficulties in that system is not being able to adjust the position of the diaphragm in relation to the valve. Consequently, the device, generally a fixed assembly, provides a widely varying initial flow rate due to manufacturing tolerances and is impossible to normalize. It would be desirable to be able to null the sensing diaphragm in test and to adjust the valve fitting for a normalized flow condition. However, in prior systems there is no way to change the initial manufactured set up of the device. Clearly, the ability to calibrate or adjust the device could insure that in-vivo performance will be as close as possible to design specifications and patient requirements.

Thus, in accordance with this invention a flexible diaphragm is incorporated in the valve design to allow for set-up and calibration adjustments to the system flow rate.

This invention will be described in greater detail by reference to the accompanying drawing and description of the preferred embodiment that follows.

Figure 1:
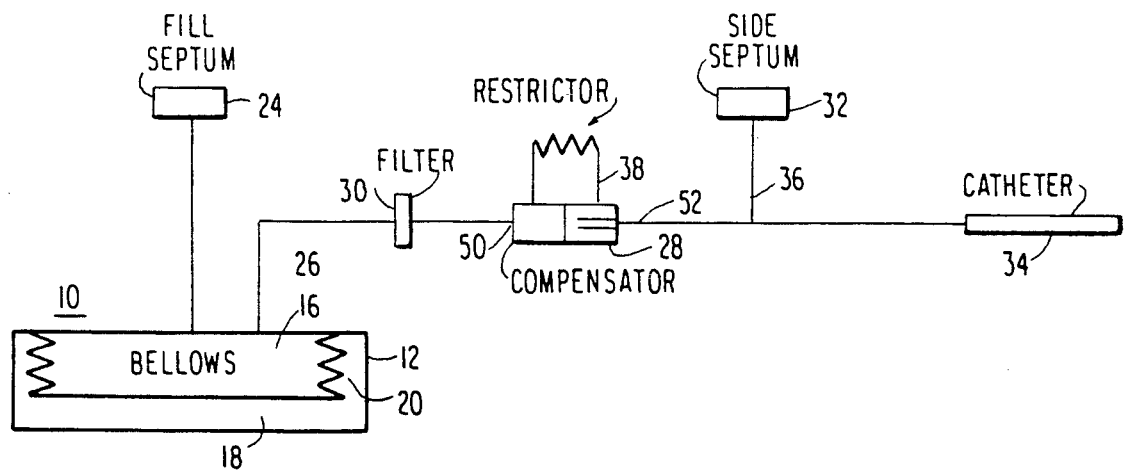
FIG. 1 is a schematic representation of the flow regulator according to this invention when used in conjunction with a pressure actuated drug delivery system.

The implantable drug delivery system is illustrated schematically in FIG. 1. It comprises an infusion pump 10 with a housing 12 divided into a drug chamber 16 and a propellant chamber 18 by means of a bellows or diaphragm 20. The infusion pump is implanted under the skin and the drug chamber may be refilled hypodermically utilizing a penetrable resilient fill septum 24. The chamber 18 contains Freon having a vapor pressure such that, under conditions of normal body temperature, creates a pressure upon the bellows 20 to force a drug contained in the chamber 16 out through the discharge opening 26, through a filter 30, to the flow rate compensator 28. In this schematic the compensator incorporates a capillary type restrictor 38.

Figure 2:
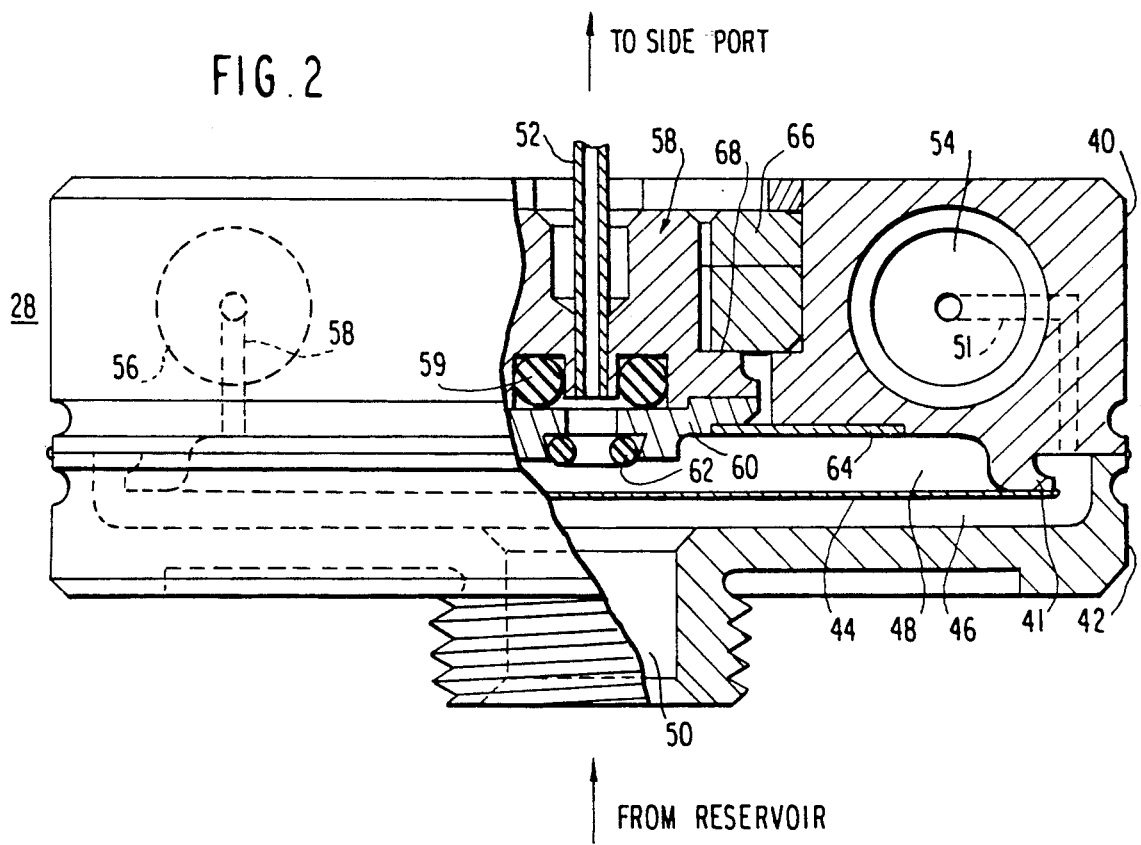
FIG. 2 is a section view of a flow rate regulator as illustrated in FIG. 1.

Referring to FIG. 2, the flow rate compensator in accordance with this invention comprises a body 28 having a top member 40 and a bottom member 42. The top portion of the bottom body member 42 and the bottom portion of the top body member 40 have flush mating surfaces at their peripheries. The resilient sensing diaphragm 44 is composed of a flexible but impervious material, such as titanium and is disposed in a cavity which the diaphragm divides into two chambers 46 and 48. The diaphragm is welded to a radial flange 41 on the top body member 40.

The top member 40 and the bottom member 42 are assembled and fastened together by any convenient means such as screws, not illustrated, welding or the like. The space in the bottom surface of the top member 48 along with the space 46 in the top of bottom body portion following assembly forms a chamber divided by the diaphragm 44.

The bottom body member 42 has an inlet passage 50 communicating with chamber 46. An outlet passage 52 connects to the flow line and to the sideport 32. As illustrated in FIG. 1, this sideport is a "T" connection into the system via passage 36. Alternatively, the outlet 52 may be in series with the sideport 32 on an in-line basis to the catheter 34.

In accordance with this invention, the inlet 50 is threaded directly onto the pump. A seal not illustrated, is placed around inlet, 50 to seal this coupling. Fluid from the drug chamber 16 flows through inlet 50 into the lower chamber 46. Via conduit 51, fluid from the lower chamber 46 is fed to an passage 54 in the upper member 40. This element provides an outlet to one side of the restrictor 38. At an opposite position on the upper member 40, a second passage 56 is disposed receiving fluid from the restrictor 38 and providing a conduit 53 to the upper chamber 48.

By this technique then, fluid is delivered unrestricted to chamber 46 and then through the restrictor 38 to chamber 48. Thus, the restrictor 38 communicates directly across the sensing diaphragm .

The outlet 52 is welded to a first portion 58 of an adjustable fitting. An O-ring 59 provides a seal in a recess of portion 58. A second portion of the adjustable fitting comprises a plate 60 having an O-ring valve 62 positioned in the recess at the lower portion thereof. A flexible diaphragm 64 is welded at its periphery in a narrow recess in the upper housing 40 and to the plate 60 comprising the second portion of the adjustable fitting. As can be appreciated then, movement of the fitting 58, 60 produces deflection in the adjustable fitting diaphragm 64.

Adjustment is by means of an internal Castle nut 66. By rotation of the castle nut 66, which bears on a flange 68 of the upper adjustable portion 58, a downward pressure is exerted causing the adjustable fitting and the adjustable fitting diaphragm 64 to be urged in a direction towards the sensing diaphragm 44. When the O-ring valve 62 contacts the titanium sensing diaphragm 44 the outlet 52 is thereby effectively sealed off. Adjustment from that sealed position is a function of movement of the Castle nut 66 so that a clearance exists between the O-ring valve 62 and the surface of the sensing diaphragm 44. By this technique, effective attenuation of the flow through 62 from chamber 48 to outlet 52 can be established and maintained automatically by the varying forces on the sensing diaphragm 44 due to changes in body temperature and atmospheric pressure.

This technique also provides for adjustment during manufacture to insure that the device is properly calibrated. Without such adjustment, the operation of the device would be a function of manufacturing tolerances which provide an inadequate basis by which to insure a predetermined regulated flow given the low volume flow rates.

In operation, medication from the drug chamber 16 is forced through the flow line 26 by the constant pressure exerted by the material in the chamber 18. The medication passing through the filter 30 is then delivered to the compensator through inlet 50. Medication flows into lower chamber 46 and via opening 54 into the restrictor 38. Then, it is delivered to the upper chamber 48 and through the outlet 52 into the catheter 34. Given the fact that there is fluid in both chambers 46 and 48, opposing forces on the diaphragm generally null the system so that the diaphragm tends to remain stationery.

If, however, there is a change in these forces, for example, as a result of a decrease in flow through the catheter 34 because of a higher atmospheric pressure, then the diaphragm 44 will be deflected downward, due to a build up of pressure in chamber 48 automatically opening O-ring valve 62 increasing flow. If, on the other hand, the pressure in chamber 48 is reduced by a lowering of atmospheric pressure such as at a higher altitude, the diaphragm will be deflected upward toward O-ring valve 62 automatically closing O-ring valve 62 reducing flow. Thus, the position of the diaphragm, which is controlled by the pressure differential between chambers 46 and 48, effectively maintains a constant or near constant flow rate through outlet 52 to catheter 34.

Given the fact that movement of the diaphragm 44 to establish a flow rate from a fully seated no flow rate condition to the desired dosage level is very small, as discussed herein adjustability of the system is required. Thus, by using the Castle nut 66 and the adjustable diaphragm feature of 60 the initial distance between the O-ring valve 62 and the diaphragm 44 can be adjusted and set to give proper flow rate. This is a material improvement over prior art systems which do not allow for such adjustability.

It is apparent that modifications and variations of this invention may be made without departing from the essential scope thereof.

Having defined my invention, I claim:

1. A drug delivery system for implantation in a living body comprising:

a pressure actuated drug delivery device having a housing, a movable member dividing said housing into two compartments, a first compartment containing a drug to be dispensed and a second compartment containing a material exerting pressure on said movable member, means for providing access to said first compartment for refilling it with a drug;

an adjustable pressure sensitive flow regulator connected to said first compartment, said flow regulator comprising a body, an inlet from said first compartment and an outlet to a catheter said outlet mounted in said body and movable thereto, a cavity divided by a flexible sensing member to define two chambers, one chamber on each side of said flexible sensing member, means to establish fluid communication between said two chambers, one of said chambers in fluid communication with said outlet, said means to move said outlet with respect to said flexible sensing member for adjusting the flow rate to said outlet from said other of said chambers such that said regulator flow is variably adjustable to any predetermined rate.

2. The drug delivery system of claim 1 further comprising a first movable fitting having a flange, said outlet comprising a stem fitted to said first movable fitting, a second movable fitting loosely coupled to said first movable fitting and tightly attached to said body allowing movement substantially perpendicular said flexible sensing member, said second movable fitting housing an O-ring seated to contact said flexible sensing member and close off said outlet when said means to move has been adjusted, and said means to move comprising an adjusting nut mounted in said body and contacting said flange on said first movable fitting, whereby movement of said nut positions said first and second movable fittings and said O-ring relative to said flexible sensing member.

3. The drug delivery system of claim 1, wherein said flexible sensing member is a metallic diaphragm mounted in said body, said metallic diaphragm movable in response to a pressure differential between said first and said second chambers.

4. The drug delivery system of claim 2 further comprising an adjustable sealing diaphragm mounted to said second movable fitting and to said body, said adjustable sealing diaphragm movable in response to movement of said adjusting nut to maintain a seal in said first cavity.

5. The drug delivery system of claim 1, wherein said regulator body comprises a pair of body components, one of said components having said inlet and a hollow portion defining one of said chambers, the other of said components having said outlet and said means to establish fluid communication contained therein, and means to join said pair of body components together in a sealed manner.

6. The drug delivery system of claim 5, wherein the other of said components comprises a depending flange, said flexible member being mounted on said flange.

* * * * *